May 14, 1940. W. KORDES Plant Pat. 395
ROSE PLANT
Filed Aug. 10, 1939
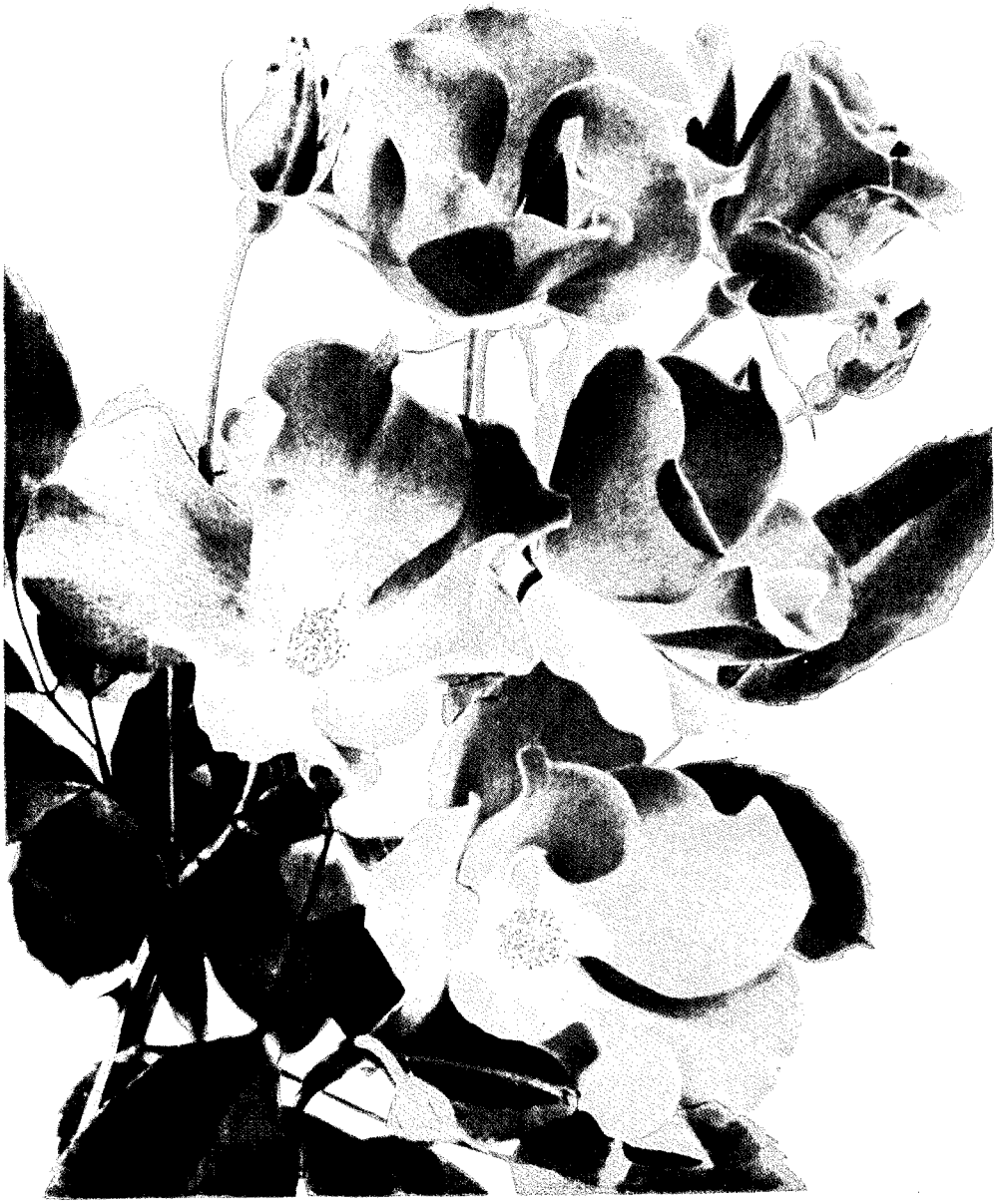
Inventor
Wilhelm Kordes
By Robert Robb
attorney Patented May 14, 1940

UNITED STATES PATENT OFFICE

395

ROSE PLANT

Wilhelm Kordes, Sparrieshoop in Holstein, Germany, assignor to Jackson & Perkins Company, Newark, N. Y.

Application August 10, 1939, Serial No. 289,488

1 Claim. (Cl. 47—61)

The present invention relates to a new and distinct variety of rose plant of the large flowered polyantha class, the result of a definite effort to produce a free flowering and hardy rose.

As a result of certain crosses, I have produced a very vigorous hardy variety characterized by the large heads of single flowers of a brilliant Carmine to Spectrum Red with a light almost white circle at the very center of each flower.

Other features of novelty reside in the long lasting quality of the flowers, the absence of any indication of bluing at any stage, the clean dropping off of the blooms at the finish, and the continuity of blooming throughout the summer season.

The foliage is disease resistant and very attractive at all times.

The following is a detailed description of the new variety, all color terminology being in accordance with Ridgway's Color Standard.

Parentage:

*Seed parent.*—Else Poulsen × (Gartendirektor Nose × Ami Quinard).

*Pollen parent.*—Dance of Joy.

Classification:

*Botanic.*—Large flowered polyantha.

*Commercial.*—Floribunda.

*Flower*

(Observations made at Newark, New York, in the morning of June 30, 1938.)

Blooming habit: Recurrent—continuous.

Bud:

*Size.*—Small.

*Form.*—Long. Is not affected by wet or hot weather.

*Color.*—When sepals first divide—Carmine, Plate 1. When petals begin to unfurl—Carmine to Ox Blood Red, Plate 1. When half blown: inside of petals—Carmine, Plate 1; reverse of petals—Carmine to Ox Blood Red, Plate 1.

*Sepals.*—Branched. Curl back when half open.

*Calyx.*—Shape—cup. Size—small. Aspect—smooth.

*Peduncle.* — Length — medium. Aspect—smooth. Color—Biscay Green, Plate 17. Strength—stiff, slender.

*Opening.*—Bud opens well. Is not affected by adverse conditions.

Bloom:

*Size.*—Medium. Average size when fully expanded—3½″.

*Borne.*—In clusters, flat.

*Stems.*—Medium length, normal.

*Form.*—When first open—high center. Permanence—flattens.

*Petalage.*—Single (one row of petals, 4 to 6). Number of petals under normal conditions—5–6.

*Color.*—Center of flower—Carmine, Plate 1. Base of petals (aiglet)—Sulphur Yellow, Plate 5. Inside of petals—Spectrum Red, to Carmine, Plate 1. Reverse of petals—Carmine, Plate 1. General tonality for a distance—Red.

*Discoloration.*—General tonality at end of first day—Carmine, Plate 1. Second day—Carmine to Spectrum Red, Plate 1. Third day—Carmine to Spectrum Red, Plate 1.

Petals:

*Texture.*—Leathery. Is not affected by wet or hot weather.

*Appearance.* — Inside — velvety. Outside — satiny.

*Form.*—Notched.

*Arrangement.*—Irregular. Petaloids in center—none.

*Persistence.*—Drop off cleanly.

*Fragrance.*—Slight. Nature—fruity (Russet apple).

*Lasting quality.*—On the plant and as cut flower—long.

Genital organs:

*Stamens, anthers.* — Size — medium, many. Color—Buff Yellow, Plate 4. Arrangement—regular around styles.

*Stamens, filaments (threads).*—Long. Color—Geranium Pink, Plate 1.

*Pollen.*—Maize Yellow, Plate 4.

*Styles.*—Columnar, uneven length, long, thin.

*Stigmas.*—Light Green Yellow, Plate 5.

*Ovaries.*—All enclosed in calyx.

Fruit: Variety is fertile with its own pollen.

*Form.*—Depressed top.

*Aspect.*—Smooth.

*Sepals.*—Permanent; recurved, curled.

*Plant*

Form: Bush.

Growth: Very vigorous, upright.

Foliage: 5–7 leaflets.

*Size.*—Medium.

*Quantity.*—Normal.

*Color.*—New foliage: upper side—Cress Green, Plate 31; under side—Light Cress Green, Plate 31. Old foliage: upper side—Yew Green, Plate 31; under side—Cress Green, Plate 31.

*Shape.*—Oval pointed.

*Texture.*—Upper side—smooth; under side—smooth. Ribs and veins—ordinary.

*Edge.*—Serrated (saw toothed).

*Serration.*—Single; large.

*Rachis.*—Color—Hay's Russet, Plate 14. Under side—smooth.

*Stipules.*—Medium length, bearded.

*Disease resistance.*—Resistant.

Wood:

*New wood.*—Color—Jade Green, Plate 31. Bark—smooth.

*Old wood.*—Color—Cress Green, Plate 31. Bark—smooth.

Thorns (thorns are divided into thorns, prickles, and short needles):

*Thorns.*—Quantity on main stalks from base—few; on laterals from stalk—few. Form—narrow base, hooked downward. Color when young—Hay's Russet, Plate 14. Position—irregular.

*Prickles.*—Quantity on main stalks and on laterals—few. Color—Hay's Russet, Plate 14.

The plant has been asexually reproduced and its distinguishing characteristics have been found to be fixed.

I claim:

A new and distinct variety of large flowering polyantha rose plant, characterized as to novelty by vigor of growth, its hardiness and resistance to disease, continuity of free flowering, the attractive coloring of its large flowers, and absence of bluing at any stage, substantially as shown and described.

WILHELM KORDES.